United States Patent [19]

Cousins et al.

[11] Patent Number: 4,996,214
[45] Date of Patent: Feb. 26, 1991

[54] QUINOLINYL SUBSTITUTED PHENYL/THIOALKANOIC ACID SUBSTITUTED PROPIONIC ACIDS AND LEUCOTRIENE ANTAGONIST USE THEREOF

[75] Inventors: Russell D. Cousins, Oxford, Pa.; James S. Frazee, Sewell, N.J.; John G. Gleason, Downington; Ralph F. Hall, Villanova, both of Pa.

[73] Assignee: SmithKline Beecham Corporation, Philadelphia, Pa.

[21] Appl. No.: 545,258

[22] Filed: Jun. 28, 1990

[51] Int. Cl.$^5$ .................. A61K 31/41; A61K 31/47; C07D 401/06; C07D 215/14
[52] U.S. Cl. .................. 514/311; 514/314; 546/172; 546/174; 546/175
[58] Field of Search ............ 546/174, 175, 172; 514/311, 314

[56] References Cited

U.S. PATENT DOCUMENTS 4,599,345  7/1986  Salamon et al. .......... 514/311
4,929,626  5/1990  Mohrs et al. .......... 546/174

*Primary Examiner*—David B. Springer
*Attorney, Agent, or Firm*—James M. Kanagy; Stuart R. Suter; Edward T. Lentz

[57] ABSTRACT

This invention covers quinolinyl substituted phenyl/thioalkanoic acid substituted propionic acids leucotriene inhibitors having the following general formula

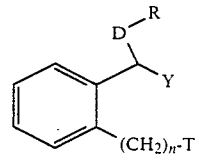

where the substituents are defined herein.

20 Claims, No Drawings

QUINOLINYL SUBSTITUTED PHENYL/THIOALKANOIC ACID SUBSTITUTED PROPIONIC ACIDS AND LEUCOTRIENE ANTAGONIST USE THEREOF

SCOPE OF THE INVENTION

This invention relates to quinolinyl substituted thioalkanoic acid derivatives which are useful for treating diseases associated with leukotrienes.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

Leukotrienenes are a group of eicosanoids formed from arachidonic acid metabolism via the lipoxygenase pathway. These lipid derivatives originate from $LTA_4$ and are of two types: (1) those containing a sulfidopeptide side chain ($LTC_4$, $LTD_4$, and $LTE_4$), and (2) those that are nonpeptidic ($LTB_4$). Leukotrienes comprise a group of naturally occuring substances that have the potential to contribute significantly to the pathogensis of a variety of inflammatory and ischemic disorders.

As summarized by Lefer, A. M., *Biochemical Pharmacology*, 35, 2, 123–127 (1986) both the peptide and nonpeptide leukotrienes exert microcirculatory actions, promoting leakage of fluid across the capillary endothelial membrane in most types of vascular beds. $LTB_4$ has potent chemotatic actions and contributes to the recruitment and adherence of mobile scavenger cells to endothelial membrane. $LTC_4$, $LTD_4$ and $LTE_4$ stimulate a variety of types of muscles. $LTC_4$ and $LTD_4$ are potent bronchoconstrictors and effective stimulators of vascular smooth muscle. This vasoconstrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. $LTC_4$ and $LTD_4$ have been shown to be potent and selective peripheral airway agonists, being more active than histamine. [See Drazen, J. M. et al., *Proc. Nat'l. Acad. Sci. U.S.A.*, 77, 7, 4354–4358 (1980)]. $LTC_4$ and $LTD_4$ have been shown to increase the release of mucous from human airways in vitro. [See Marom, Z. et al., Am. Rev. Respir. Dis., 126, 449–451 (1982).] The leukotriene antagonists of the present invention can be useful in the treatment of allergic or non-allergic bronchial asthma or plumonary anaphylaxis.

Leukotrienes have been identified in the nasal secretions of allergic subjects who underwent in vivo challenge with specific antigen. The release of the leukotrienes was correlated with typical allergic signs and symptoms. [See Creticos, P. S. et al., *New England J. of Med.*, 310, 25, 1626–1629 (1984). This suggests that allergic rhinitis is another area of utility for leukotriene antagonists.

Leukotrienes have also been directly or indirectly implicated in a variety of non-pulmonary diseases in the ocular, dermatologic, cardiovascular, renal, trauma, inflammatory, carcinogenic and other areas.

Leukotriene antagonists can also be useful in the area of renal ischemia or renal failure. Badr et al. have shown that $LTC_4$ produces significant elevation of mean arterial pressure and reductions in cardiac output and renal blood flow, and that such effects can be abolished by a specific leukotriene antagonist. [See Badr, K. F. et al., *Circulation Research*, 54, 5, 492–499 (1984). Leukotrienes have also been shown to have a role in endotoxin enduced renal failure and the effects of the leukotrienes selectively antagonized in this model of renal injury. [See Badr, K. F. et al., *Kideny International*, 30, 474–480 (1986).] $LTD_4$ has been shown to produce local glomerular constrictor actions which are prevented by treatment with a leukotriene antagonist, [See Badr, K. F. et al., *Kidney International*, 29, 1, 328 (1986). $LTC_4$ has been demonstrated to contract rat glomerular mesangial cells in culture and thereby effect intraglomerular actions to reduce filtration surface area. [See Dunn, M. J. et al., *Kidney International*, 27, 1, 256 (1985). Thus another area of utility for leukotriene antagonists can be in the treatment of glomerulonephritis.

Cysteinyl leukotrienes have also been shown to undergo enterohepatic circulation, and thus are indicated in the area of inflammatory liver disease. [See Denzlinger, C. et al., *Prostaglandins Leukotrienes and Medicine*, 21, 321–322 (1986). Leukotrienes can also be important mediators of inflammation in inflammatory bowel disease. [See Peskar, B. M. et al., *Agents and Actions*, 18, 381–383 (1986).] Leukotriene antagonists thus can be useful in the treatment of inflammatory liver and bowel disease.

By antagonizing the effects of $LTC_4$, $LTD_4$ and $LTE_4$ or other pharmacologically active mediators at the end organ, for example airway smooth muscle, the compounds and pharmaceutical compositions of the instant invention are valuable in the treatment of diseases in subjects, including human or animals, in which leukotrienes are a key factor.

Leukotriene antagonists based on 3-phenyl-3-carboxyalkylthioalkanoic acids are disclosed in U.S. Pat. No. 4,820,719.

SUMMARY OF THE INVENTION

In a first aspect, this invention relates to compounds of formula

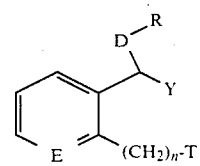

or a pharmaceutically acceptable salt thereof wherein
E is CH or N;
D is O or $S(O)_q$ where q is 0, 1 or 2;
R is $-(CH_2)_nA$, $-(CH_2)_nArA$ or ArA where n is 1–4, Ar is phenyl or substituted phenyl, thienyl, pyridyl, imidazolyl, tetrazol-5-yl or thiazolyl and A is $-(CH_2)_nR_2$, $-R_2$, -tetrazol-5-yl, $-CH(NH_2)R_2$, $-CN$, $-SO_3H$, $-SO_2NH_2$, $NHSO_2R_6$—$CH(NH_2)COR_4$, or $-CONHCH_2COR_4$;
Y is $R_2$, $CH(R_3)(CH_2)_mR_2$, $CH(R_3)$-tetrazol-5-yl, or tetrazol-5-yl;
m is 0, 1, and 2;

$R_3$ is hydrogen, $C_1$ to $C_4$ alkoxy, fluoro or hydroxy;

$R_2$ is —$COR_4$ where $R_4$ is —OH, —OE where E is a pharmaceutically acceptable cation or a pharmaceutically acceptable ester-forming group, $R_2$ is —$CON(R_5)_2$ where $R_5$ is H, $C_1$ to $C_6$ alkyl, phenyl$C_1$-$C_6$-alkyl, or the two $R_5$ groups are combined to form a cyclic group having 3 to 5 carbons, —CN, —$SO_3H$, —$SO_2NH_2$, $NHSO_2R_6$, —$CH(NH_2)COR_4$, or —$CONHCH_2COR_4$;

$R_6$ is $C_1$ to $C_{10}$-alkyl, phenyl, or phenyl$C_1$ to $C_3$-alkyl.

n is 4–11; and

T is halosubstituted quinolyl.

This invention also relates to a means for treating diseases pulmonary or non-pulmonary diseases which involve leukotrienes and which can be treated by administering a leukotriene antagonist.

Also within the scope of this invention are pharmaceutical compositions which comprise a compound of formula I either alone or formulated with a pharmaceutically acceptable excipient. Such compositions may also contain an $H_1$ blocker.

DETAILED DESCRIPTION OF THE INVENTION

The following definitions are used in describing this invention and setting out what the inventors believe to be their invention herein.

"Halo" refers to and means fluoro, chloro, bromo or iodo. The quinolyl ring may be substituted with one or more of these radicals. Multiple substituents may be the same or different, such as where there are three chloro groups, or a combination of chloro and alkyl groups and further where this latter combination may have different alkyl radical in the chloro/alkyl substituent pattern.

The phase "a pharmaceutically acceptable ester-forming group" in $R_2$ and $R_3$ covers all esters which can be made from the acid function(s) which may be present in these compounds. The resultant esters will be ones which are acceptable in their application to a pharmaceutical use. By that it is meant that the esters, which can be mono- or diesters, will retain the biological activity of the parent compound and will not have an untoward or deleterious effect in their application and use in treating diseases. Such esters are, for example, those formed with one of the following radicals representing $R_5$: $C_1$ to $C_{10}$ alkyl, phenyl $C_1$-$C_6$alkyl, a cyclic group of 3 to 7 carbons, cycloalkyl, aryl, arylalkyl, alkylaryl, alkylarylalkyl, aminoalkyl, indanyl, pivaloyloxymethyl, acetoxymethyl, propionyloxymethyl, glycyloxymethyl, phenylglycyloxymethyl, or thienylglycyloxymethyl. Aryl includes phenyl and naththyl, or heteroaromatic radicals like furyl, thienyl, imidazolyl, triazolyl or tetrazolyl. The most preferred ester-forming radicals are those where $R_5$ is alkyl, particularly alkyl of 1 to 10 carbons, [i.e. $CH_3$—$(CH_2)_n$— where n is 0–9], or phenyl—$(CH_2)_n$— where n is 0–4.

Amides may be formed from any of the acid groups which may be present in these compounds. Such amides may be mono- or disubstituted. The most preferred amides are those where both —$R_5$ groups are hydrogen or n-alkyl of 1 to 6 carbon atoms, particularly diethylamide.

Pharmaceutically acceptable salts of the instant compounds are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner in a suitable solvent from the parent compound an an excess of an organic or inorganic acid, in the case of acid addition salts, or an excess of organic or inorganic base. Representative acids are hydrochloric acid, hydrobromic acid, sulfuric acid, phosphoric acid, acetic acid, maleic acid, succinic acid or methanesulfonic acid. Cationic salts are readily prepared from alkali metal bases such as sodium, potassium, calcium, magnesium, zinc, copper or the like and ammonia. Organic bases include the mono or disubstituted amines, amino acids, caffeine, tromethamine, tris compounds, ethylenediamine, triethylamine, piperazine and the like.

If by some combination of substituents, a chiral center is created or another form of an isomeric center is created in a compound of this invention, all forms of such isomer(s) are intended to be covered herein. Compounds with a chiral center may be administered as a racemic mixture or the racemates may be separated and the individual enantiomer used alone.

The preferred compounds of this invention are those where E is CH, D is —S— or —O—; R is —$CH_2CH_2R_2$, —$CH_2ArR_2$, or $ArR_2$; $R_2$ is $CO_2R_4$, Y is $CH_2R_2$, or $CH(R_3)(CH_2)_mR_2$ where $R_3$ is H, —OH or —$OCH_3$ and m is 0, n is 4–11, and T is 7-halosubstituted quinolyl. Another preferred group os compounds are those E is N, D is —S—, R is —$CH_2CH_2R_2$, Y is $CH_2R_2$, and n is 4–11. The more preferred compounds of either of the two foregoing groupings are those compounds where n is 7 and T is 7-chloroquinol-2-yl. The most preferred compound are:

3-{2-[7-(7-chloro)quinolin-2-yl)heptyl]phenyl}-3,3'-thiodipropionic acid, 2-hydroxy-3-{2-[7-(2-(7-chloro)quinolinyl)heptyl]phenyl}-3,3'-thiodipropionic acid;

3-{2-[7-(7-chloro)quinolin-2-yl)heptyl]pyridyl}-3,3'-thiodipropionic acid, and.

2-hydroxy-3-{2-[7-(2-(7-chloro)quinolinyl)heptyl]pyridyl}-3,3'-thiodipropionic acid.

These compounds may be prepared by a series of synthetic steps which begin with 2-bromobenzaldehyde or the corresponding 2-bromopyridyl compound. This sequence of steps is outlined in the following flow chart. It is intended to illustrate the general case by means of the specific reagents and intermediates recited in this scheme.

Reaction Scheme

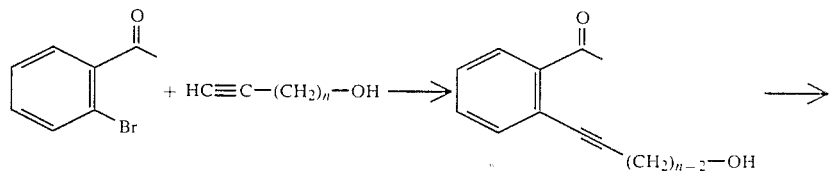

Reaction Scheme -continued

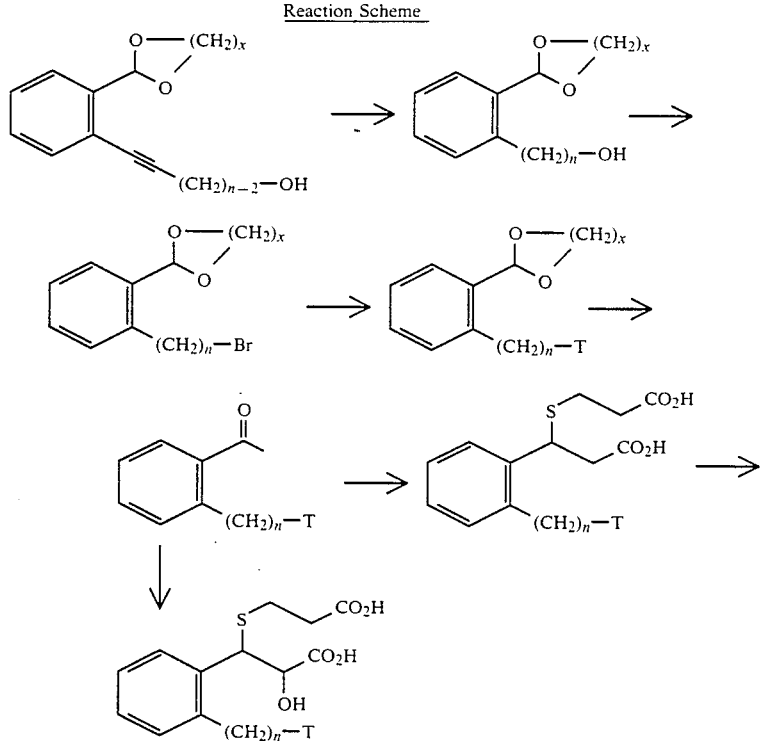

The 2-bromobenzaldehyde starting material is a known compound. It is coupled with a 1-alkynol where the OH group is on the ω carbon in the presence of cuporous iodide and $(P\phi_3)_2PdCl$. This follows the procedure of Hagihara, et al. *Synthesis*, 627, (1980). The aldehyde group is then protected by some means in preparation for carrying out the next several reactions. In this scheme, an acetal is formed, a dioxolane, using a dihydroxy compound such as ethylene glycol. The reaction is effected using a strong acid such as p-toluenesulfonic acid.

With the carbonyl group protected, the triple bond is reduced by catalytic hydrogenation. The terminal hydroxy group is then converted to a halo moiety by means of triphenylphosphine and carbontetrahalide; in this case carbontetrabromide is illustrated. This halo group is then displaced in the process of adding the T group. A quinolinyl radical is added using a strong base to effect the reaction. This reaction is best done under an inert atmosphere at reduced temperature. It affords the 2-quinolinyl compound.

Once the $R_1$ group is in place, the aldehyde function is utilized to introduce the thiodipropionic acid group, or a related group. First, the dioxolane is hydrolyzed using acid. Mineral acid is preferred. This aldehyde then becomes the starting point for going one of several ways to the desired product, a compound of formula I.

Where Y is $R_2$, the compound can be prepared directly from the aldehyde.

For compounds where Y is $CH_2(CH_2)_mR_2$ the cinnamate or its homolog is first prepared then treated with the appropriate mercaptan to introduce the thiol group into the molecule. Where $R_3$ is —OH, an epoxide is first prepared by mixing the aldehyde with methyl chloroalkanoate or a similar ester and adding sodium methoxide. This reaction is best carried out under an inert atmosphere. The resulting ester is then hydrolyzed, preferably with base, before being being treated with a mercaptan to obtain the 2-hydroxythiodipropionic acid; a homolog is obtained by varying the reactants appropriately.

Esters made according to the foregoing scheme may be hydrolyzed with base to obtain the desired acid salt, or the basic hydrolysis solution can be acidified to obtain the free acid. For example, an ester can be saponified by dissolving it in an appropriate solvent, adding a molar excess of an alkali metal base, for example lithium hydroxide or potassium hydroxide. This solution is stirred for a period of time, e.g. 15 minutes to overnight. If the salt is the intended final product, the hydrolysate is worked up at that point. The acid is obtained by acidifying the solution and recovering the acid by appropriate means.

Amides may be formed by any appropriate amidation reaction. One way to prepare such compounds is to convert an acid to an acid chloride and then treat that compound with ammonium hydroxide or an appropriate mono- or disubstituted amine. For example, the acid is treated with an alchholic base solution such an ethanol/KOH at room temperature for about 30 minutes. The solvent is removed and the residue taken up in an organic solvent such as diethyl ether, treated with a dialkyl formamide and then a 10-fold excess of oxalyl chloride. This may be effected at a moderately reduced temperature, for example between $-10°$ and $+10°$. This solution is stirred at reduced temperature for 1-4 hours. Solvent is then removed and the residue taken up in an inert solvent (e.g. benzene) and treated with concentrated ammonium hydroxide. This solution may be cooled in an ice bath. After 1-4 hours, the amide is recovered by conventional means.

Assays

The leukotriene antagonist activity of the compounds of this invention was measured by the ability of the compounds to inhibit the leukotriene induced contraction of guinea pig tracheal tissues in vitro. The following methodology was employed: In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hour, pretreated for 15 minutes with meclofenamic acid (1 mM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize inter-tissue variability, the contractions elicited by $LTD_4$ were standardized as a percentage of the maximum response obtained to a reference agonist, carbachol (10 mM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The -log $K_B$ value for the test compound was determined by the following equations:

$$X = \text{Dose ratio} = \frac{EC_{30} \text{ (presence of test compound)}}{EC_{30} \text{ (presence of vehicle control)}} \quad 1.$$

$$K_B = \text{concentration of test compound}/(X-1) \quad 2.$$

The compounds of this invention possess useful antagonist activity against leukotrienes, primarily leukotriene $D_4$. The antagonist activity of representative compounds of this invention is tabulated below. The -log $K_B$ values were calculated from the above test protocols. A representative compound, the phenylpentyl-substituted analog, was compared in this assay to the known leukotriene antagonist 2-hydroxy-3-(2-carboxyethylthio)-3-((2-octylphenyl)phenyl)propionic acid. In this assay, 3-{2-[7-(7-chloro)quinolin-2-yl]heptyl]-phenyl}-3,3'-thiodipropionic acid gave a $pK_B$ of 7.5 and a $K_i$ of 7.7 nmole Pharmaceutical compositions of the present invention comprise a pharmaceutical carrier or diluent and an amount of a compound of the formula (I) or a pharmaceutically acceptable salt, such as an alkali metal salt thereof, sufficient to produce the inhibition of the effects of leukotrienes.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, whether it be parenterally, topically, orally or by inhalation.

In general, particularly for the prophylactic treatment of asthma, the compositions will be in a form suitable for administration by inhalation. Thus the compositions will comprise a suspension of solution of the active ingredient in water for administration by means of a conventional nebulizer. Alternatively the compositions will comprise a suspension or solution of the active ingredient in a conventional liquified propellant or compressed gas to the administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient. The drug may also be administered as an aerosol.

For parenteral administration the pharmaceutical composition may be in the form of a sterile injectable liquid such as an ampule or an aqueous or nonaqueous liquid suspension.

For topical administration the pharmaceutical composition may be in the form of a cream, ointment, liniment, lotion, pastes, and drops suitable for administration to the eye, ear, or nose.

For oral administration the pharmaceutical composition will be in the form of a tablet, capsule, powder, pellet, atroche, lozenge, syrup, liquid, or emulsion.

Sustained release formulations may also be prepared. Reference is made to the reference book *Remington's Pharmaceutical Sciences* for detailed information on the preparation of such formulations, and for assistance in preparing all other formulations indicated by the practice of this invention.

Usually a compound of formula I is administered to a subject in a composition comprising a therapeutically effective amount, a nontoxic amount, sufficient to produce an inhibition of the symptoms of a disease in which leukotrienes are a factor. When employed in this manner, the dosage of the composition is selected from the range of from 250 mg to 700 mg of active ingredient for each administration. For convenience, equal doses will be administered 1 to 5 times daily with the daily dosage regimen being selected from about 250 mg to about 2800 mg.

The pharmaceutical preparations thus described are made following the conventional techniques of the pharmaceutical chemist as appropriate to the desired end product.

Included within the scope of this disclosure is the method of treating a disease comprising administering to a subject a therapeutically effective amount of a compound of formula I, preferably in the form of a pharmaceutical composition. For example, inhibiting the symptoms of an allergic response resulting from a mediator release by administration of an effective amount of a compound of formula I is included within the scope of this disclosure. The administration may be carried out in dosage units a suitable intervals or in single doses as needed. Usually this method will be practiced when relief of symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the condition or disease being treated, and so forth.

Compounds of this invention, alone and in combination with a histamine $H_1$-receptor antagonist, inhibit antigen-induced contraction of isolated, sensitized guinea pig trachea (a model of respiratory anaphylaxis as described by Weichman, B. M., Wasserman, M. A., Holden, D. A., Osborn, R. R., Woodward, D. F., Ku, T. W., and Gleason, J. G., *J. Pharmacol. Exp. Ther.*, 227, 700–705, 1983).

Pharmaceutical compositions and their method of use also include the combination of a compound of formula I with $H_1$ blockers where the combination contains sufficient amounts of both compounds to treat antigen-induced respiratory anaphylaxis or similar allergic reaction. Representative $H_1$ blockers useful here include: cromolym sodium, compounds from the ethanolamines class (diphenhydramine), ethylenediamines (pyrilamine), the alkylamine class (chlorpheniramine), the piperazine class (chlorcyclizine), and the phenothiazine class (promethazine). $H_1$ blockers such as 2-[4-(5-bromo-3-methylpyrid-2-yl)butylamino]-5-[(6-methylpyrid-3-yl)methyl]-4-pyrimidone are particularly useful in this invention.

EXAMPLES

The following are a set of examples given to illustrate how to make and use the compounds of this invention. These Examples are just that, examples, and are not intended to circumscribe or otherwise limit the scope of this invention. Reference is made ot the claims for defining what is reserved to the inventors by this document.

EXAMPLE 1

3-{2-[7-(2-(7-Chloro)quinolinyl)heptyl]phenyl}-3,3'-thiodipropionic acid

1(a) 2-(6-Hydroxyhex-1-ynyl)benzaldehyde. To a solution of 2-bromobenzaldehyde (5.0 g, 27.0 mmol) and 5-hexyn-1-ol (3.18 g, 32.0 mmol) in triethyl amine (100 mL) was added bis(triphenylphosphine)palladium (II) dichloride (0.28 g, 0.4 mmol) and cuprous iodide (51 mg, 0.27 mmol). After heating the resulting mixture to reflux under an argon atmosphere for 1 hour, the reaction mixture was allowed to cool to room temperature and filtered. The filtrate was concentrated in vacuo, and the residue was purified by silica gel chromatography eluting with 2:1 diethyl ether/hexanes to afford a yellow oil.

90 MHz $^1$H NMR (CDCl$_3$): $\delta$ 10.55 (s, 1H); 7.90 (d, 1H, J=7 Hz); 7.45 (m, 3H); 3.75 (t, 2H, J=3 Hz); 2.50 (m, 2H); 2.45 (br s, 1H); 1.75 (m, 4H). IR (neat, cm$^{-1}$): 3380, 2950, 2240, 1700.

1(b) 2-{2-[(6-Hydroxyhex-1-ynyl)phenyl]}-1,3-dioxolane. To a solution of 2-(6-hydroxyhex-1-ynyl)benzaldehyde (3.95 g, 22.0 mmol) in benzene (70 mL) was added ethylene glycol (1.46 g, 24.0 mmol) and p-toluenesulfonic acid (10 mg). The resulting solution was heated to reflux overnight under an argon atmosphere azeotropic removal of H$_2$O. The reaction mixture was concentrated under reduced pressure. The residue was dissolved in CH$_2$Cl$_2$, washed with aqueous NaHCO$_3$ and dried (MgSO$_4$). Removal of the solvent in vacuo and purification of the residue using silica gel chromatography eluting with 70% diethyl ether/hexanes provided a colorless oil.

90 MHz $^1$H NMR (CDCl$_3$): $\delta$ 7.70–7.15 (m, 4H); 6.25 (s, 1H); 4.10 (m, 4H); 3.65 (m, 2H); 2.50 (m, 2H); 2.15 (br, s, 1H); 1.70 (m, 4H). IR (neat, cm$^{-1}$): 3400, 2950, 2240.

1(c) 2-{2-[(6-Hydroxyhexyl)phenyl]}-1,3-dioxolane. 2-{2-[(6-Hydroxyhex-1-ynyl)phenyl]}-1,3-dioxolane (3.4 g, 13.8 mmol) in tetrahydrofuran (80 mL) was treated with 5% Pd/C (0.5 g) and shaken on a Parr hydrogenator at 55 psi H$_2$ for 1 hour. Magnesium sulfate (2 g) was added, and the mixture was filtered. The filtrate was concentrated under reduced pressure to provide a colorless oil.

90 MHz $^1$H NMR (CDCl$_3$): $\delta$ 7.55 (m, 1H); 7.20 (m, 3H); 5.97 (s, 1H); 4.12 (m, 4H); 3.60 (t, 2H, J=6 Hz); 2.72 (t, 2H, J=8 Hz); 2.05 (s, 1H); 1.80–1.30 (m, 8H). IR (neat, cm$^{-1}$): 3400, 2940.

1(d) 2-{2-[(6-Bromohexyl)phenyl]}-1,3-dioxolane. To a solution of 2-{2-[(6-hydroxyhexyl)phenyl]}-1,3-dioxolane (1.1 g, 4.4 mmol) and triphenylphosphine (1.5 g, 6.0 mmol) in CH$_2$Cl$_2$ (11 mL) at 0° C. under an argon atmosphere was added a solution of CBr$_4$ (1.9 g, 6.0 mmol) in CH$_2$Cl$_2$ (5 mL). The resulting mixture was allowed to warm to room temperature and stirred overnight. The mixture was concentrated in vacuo, and the residue was purified by chromatography using silica gel which had been slurried in 1% triethyl amine/2% diethyl ether/hexanes to afford a yellow oil.

90 MHz $^1$H NMR (CDCl$_3$): $\delta$ 7.55 (m, 1H); 7.20 (m, 3H); 6.00 (s, 1H); 4.10 (m, 4H); 3.40 (t, 2H, J=6 Hz); 2.70 (t, 2H, J=8 Hz); 2.00–1.20 (m, 8H).

1(e) 7-Chloro-2-{7-[2-(2-(1,3-dioxolanyl)phenyl)-heptyl]}quinoline. To a solution of N,N-diisopropyl amine (0.32 g, 3.0 mmol) in tetrahydrofuran (5 mL) at −20° C. under an argon atmosphere was added dropwise n-butyl lithium (1.3 mL of a 2.5M solution in hexanes, 3.0 mmol). A solution of 7-chloroquinaldine (0.57 g, 3.0 mmol) in tetrahydrofuran (2 mL) was added to this dropwise, and the resulting deep orange solution was stirred at −20° C. for 10 min. To this was added dropwise a solution of 2-{2-[(6-bromohexyl)phenyl]}-1,3-dioxolane (1.0 g, 3.0 mmol) in tetrahydrofuran (2 mL). The resulting solution was stirred at −20° C. for 1½ hours. The reaction mixture was partitioned between diethyl ether (30 mL) and H$_2$O (30 mL), and the organic extract was washed with saturated aqueous NaCl and dried (MgSO$_4$). Removal of the solvent in vacuo and purification of the residue by column chromatography eluting with 15% diethyl ether/hexanes provided a yellow oil.

90 MHz $^1$H NMR (CDCl$_3$): $\delta$ 8.10–7.00 (m, 9H); 5.97 (s, 1H); 4.05 (m, 4H); 2.90 (t, 2H, J=8 Hz); 2.70 (t, 2H, J=8 Hz); 2.00–1.20 (m, 10H). IR (neat, cm$^{-1}$): 2940, 1640.

1(f) 2-{7-[2-(7-Chloro)quinolinyl]heptyl}benzaldehyde. 7-Chloro-2-{7-[2-(2-(1,3-dioxolanyl)phenyl)heptyl]}quinoline (0.38 g, 0.93 mmol) was treated with 1:1 acetone/1N HCl (6 mL), and the resulting solution was stirred at room temperature for 1 hour. The acetone was removed under reduced pressure. The pH was adjusted with aqueous K$_2$CO$_3$ and the solution extracted with diethyl ether. The organic extract was washed with saturated aqueous NaCl and dried (MgSO$_4$). Removal of the solvent in vacuo provided an amber oil.

90 MHz $^1$H NMR (CDCl$_3$): δ 10.30 (s, 1H); 8.10–7.10 (m, 9H); 3.00 (t, 2H, J=6 Hz); 2.90 (t, 2H, J=8 Hz); 2.10–1.20 (m, 10H). IR (neat, cm$^{-1}$): 2930, 1700, 1620.

1(g) Methyl 2-{7-[2-(7-chloro)quinolinyl]heptyl}cinnamate. 2-{7-[2-(7-Chloro)quinolinyl]heptyl}benzaldehyde (0.31 g, 1.0 mmol) and methyl (triphenylphosphoranylidene)acetate (0.34 g, 1.2 mmol) were combined in toluene (6 mL), and the resulting solution was heated to reflux for 1½ hours under an argon atmosphere. The solvent was removed under reduced pressure, and the residue was purified by silica gel chromatography eluting with 10% ethyl ether/hexanes to afford a yellow oil.

90 MHz $^1$H NMR (CDCl$_3$): δ 8.20–7.00 (m, 10H); 6.35 (d, 1H, J=15 Hz); 3.85 (s, 3H); 2.90 (t, 2H, J=8 Hz); 2.70 (t, 2H, J=8 Hz); 2.00–1.20 (m, 10H). IR (neat, cm$^{-1}$): 1740, 1640.

1(h) Dimethyl 3-{2-[7-(2-(7-chloro)quinolinyl)heptyl]phenyl}-3,3'-thiodipropionate. To a solution of methyl 2-{7-[2-(7-chloro)quinolinyl]heptyl}cinnamate (0.24 g, 0.57 mmol) in methanol (5 mL) was added methyl 3-mercaptopropionate (0.34 g, 3.0 mmol) and triethylamine (0.57 g, 0.56 mmol). After stirring at room temperature for 2 days, the solvent was removed under reduced pressure. The residue was purified by silica gel chromatography eluting with 1:2 dietyl ether/hexanes, providing a pale yellow oil.

90 MHz $^1$H NMR (CDCl$_3$): δ 8.10–7.10 (m, 9H); 4.70 (t, 1H, J=8 Hz); 3.65 (s, 6H); 3.15–2.40 (m, 10H); 2.00–1.20 (m, 10H). IR (neat, cm$^{-1}$): 2930, 1740.

1(i) 3-{2-[7-(2-(7-Chloro)quinolinyl)heptyl]phenyl}-3,3'-thiodipropionic acid. A solution of dimethyl 3-{2-[7-(2-(7-chloro)quinolinyl)heptyl]phenyl}-3,3'-thiodipropionate (0.30 g, 0.55 mmol) in acetonitrile (4 mL) and 3N HCl (3mL) was heated to reflux for 4 hours. The solvent was removed in vacuo, and the residue was partitioned betweened H$_2$O and CHCl$_3$. The organic extract was dried (MgSO$_4$), and the solvent was removed under reduced pressure to afford a colorless oil. 90 MHz $^1$H NMR (CDCl$_3$): δ 8.20 (s, 1H); 8.05 (d, 1H, J=8 Hz); 7.65 (d, 1H, J=8 Hz); 7.50–7.00 (m, 6H); 4.70 (t, 2H, J=7 Hz); 3.15–2.40 (m, 10H); 2.00–1.20 (m, 10H).

Treatment of the foregoing diacid with a molar excess of piparazine provides a salt; m.p. 146°–149° C.

EXAMPLE 2

3-{2-[7-(2-(7-chloro)quinolinyl)heptyl]phenyl}-hydroxy-3,3'-thiodipropionic acid 2(a) Methyl {2-[7-(2-(7-chloro)quinolinyl)heptyl]phenyl}-2,3-epoxypropionate. To a solution of 2-{7-[2-(7-chloro)quinolinyl]-heptyl}benzaldehyde (0.20 g, 0.55 mmol) and methyl chloroacetate (0.08 g, 0.77 mmol) in CH$_2$Cl$_2$ (4 mL) at −10° C. under an argon atmosphere was added dropwise 25% sodium methoxide in CH$_3$OH (0.15 mL, 0.70 mmol). The resulting solution was allowed to warm to room temperature. After stirring overnight, the solution was partitioned between CH$_2$Cl$_2$ and a pH 7 buffer. The organic extract was dried (MgSO$_4$). Removal of the solvent in vacuo and purification of the residue on silica gel chromatography eluting with 20% Et$_2$O/hexanes provided a yellow oil.

90 MHz $^1$H NMR (CDCl$_3$): δ 8.05 (s, 1H); 8.00 (d, 1H, J=6 Hz); 7.65 (d, 1H, J=8 Hz); 7.45–7.00 (m, 6H); 4.28 (d, 1H, J=1 Hz); 3.82 (s, 3H); 3.40 (d, 1H, J=1 Hz); 2.95 (t, 2H, J=8 Hz); 2.70 (t, 2H, J=8 Hz); 2.00–1.20 (m, 10H).

2(b) {2-[7-(2-(7-Chloro)quinolinyl)heptyl]phenyl}-2,3-epoxypropionic acid, lithium salt. To a solution of methyl {2-[7-(2-(7-chloro)quinolinyl)heptyl]phenyl}-2,3-epoxypropionate (1.0 g, 2.3 mmol) in methanol (7 mL) was added a solution of LiOH·H$_2$O (0.29 g, 6.9 mmol) in H$_2$O (3 mL). After stirring overnight at room temperature, the methanol was removed in vacuo, and the residue was partitioned between ethyl acetate and H$_2$O. The organic extract was washed with saturated aqueous NaCl and dried (MgSO$_4$). Removal of the solvent in vacuo provided a glassy solid which was used without further purification.

2(c) 3-{2-[7-(2-(7-Chloro)quinolinyl)heptyl]phenyl}-2-hydroxy-3,3'-thiodipropionic acid. To a solution of the lithium salt of {2-[7-(2-(7-chloro)quinolinyl)heptyl]phenyl}-2,3-epoxypropionic acid (0.10 g, 0.23 mmol) in tetrahydrofuran (2 mL) at 5° C. under an argon atmosphere was added methyl 3-mercaptopropionate (0.03 g, 0.28 mmol) and 25% sodium methoxide in methanol (1 drop). After stirring at 5° C. for 2 hours, a solution of NaOH (0.03 g, 0.73 mmol) in H$_2$O (1 mL) was added, and the resulting mixture was allowed to warm to room temperature and stirred overnight. The pH was adjusted to 3 to 4 using 3N HCl, and the mixture was partitioned between ethyl acetate and H$_2$O. The organic extract was washed with saturated aqueous NaCl and dried (MgSO$_4$). Removal of the solvent in vacuo provided the captioned compound as a glassy solid.

90 MHz $^1$N HMR (acetone-d$_6$): δ 8.25 (d, 1H, J=8 Hz); 8.15 (d, 1H, J=1 Hz); 7.95 (d, 1H, J=9 Hz); 7.75 (m, 1H); 7.60–7.05 (m, 9H); 6.70 (br s, 3H); 4.75 (s, 2H); 3.10–2.50 (m, 8H); 2.00–1.20 (m, 10H).

Treatment with a molar excess of piperazine provides a salt.

EXAMPLE 4

3-{2-[7-(2-(7-Chloro)quinolinyl)heptyl]phenyl}-2-hydroxy-3-(4-methoxybenzylthio)propanoic acid 3-{2-[7-(2-(7-Chloro)quinolinyl)heptyl]phenyl}-2-hydroxy-3-(4-methoxybenzylthio)propanoic acid. To a solution of 2,3-epoxy-3-{2-[7-(2-(7-chloro)quinolinyl)heptyl]phenyl}propanoic acid, lithium salt (0.70 g, 1.6 mmol) in THF (20 mL) at 5° C. under an argon atmosphere was added 4-methoxy-a-toluenethiol (0.25 g, 1.6 mmol) followed by the dropwise addition of sodium methoxide (5 drops of 25% solution in methanol). The resulting mixture was allowed to warm to room temperature and stirred overnight. The mixture was concentrated under reduced pressure, and the residue was partitioned between ethyl acetate and dilute aqueous HCl. The organic extract was washed with saturated aqueous NaCl and dried (MgSO$_4$). The solvent was removed in vacuo, and the residue was purified by flash chromatography to provide a white solid.

250 MHz $^1$H NMR (acetone-d$_6$): δ 8.05 (s, 1H); 8.00 (d, J=5 Hz, 1H); 7.80–6.70 (m, 11H); 4.55 (d, J=4 Hz, 1H); 4.42 (d, J=4 Hz, 1H); 3.62 (s, 2H); 3.60 (s, 3H); 2.90 (t, J=7 Hz, 2H); 2.35 (t, J=7 Hz, 2H); 1.90–1.20 (m, 10H).

EXAMPLE 5

3-{2-[7-(2-(7-Chloro)quinolinyl)heptyl]phenyl}-3-(4-methoxybenzylthio)propanoic acid 5(A) Methyl 3-{2-[7-(2-(7-chloro)quinolinyl)heptyl]phenyl}-3-(4-methoxybenzylthio)propanoate. To a solution of methyl 3-{2-[7-(2-(7-chloro)quinolinyl)heptyl]-phenyl}propenoate (0.40 g, 1.0 mmol) and 4-methoxy-a-toluenethiol (0.80 g, 5.0 mmol) in methanol (5 mL) under an argon atmosphere was added triethylamine (1.0 g, 10.0 mmol). The resulting mixture was stirred at room temperature for 36 h and then concentrated under reduced pressure. The residue was purified by flash chromatography, eluting with 15% ether/hexanes to provide a colorless oil.

250 MHz $^1$H NMR (CDCl$_3$): δ 8.10–7.00 (m, 12H); 6.75 (d, J=8 Hz, 2H); 4.50 (t, J=7 Hz, 1H); 3.70 (s, 3H); 3.55 (two overlapping s, 5H); 2.90 (m, 4H); 2.50 (t, J=8 Hz, 2H); 2.00–1.20 (m, 10H).

5(B) 3-{2-[7-(2-(7-Chloro)quinolinyl)heptyl]phenyl}-3-(4-methoxybenzylthio)propanoic acid. To a solution of methyl 3-{2-[7-(2-(7-chloro)quinolinyl)heptyl]-phenyl}-3-(4-methoxybenzylthio)propanoate (0.10 g, 0.20 mmol) in CH$_3$CN (1 mL) was added 3N HCl (1 mL), and the resulting mixture was heated at reflux for 4 h. The mixture was allowed to cool and was concentrated under reduced pressure. The residue was partitioned between CH$_2$Cl$_2$ and water. The organic extract was dried (MgSO$_4$) and concentrated in vacuo to provide a glassy solid.

250 MHz $^1$H NMR (CDCl$_3$): δ 10.60 (br s, 1H); 8.30 (s, 1H); 8.05 (d, J=9 Hz, 1H); 7.70 (d, J=9 Hz, 1H); 7.60–6.90 (m, 9H); 6.65 (d, J=12 Hz, 1H); 4.60 (t, J=8 Hz, 1H); 3.65 (s, 3H); 3.60 (s, 2H); 2.95 (m, 4H); 2.45 (m, 2H); 1.80–1.20 (m, 10H).

EXAMPLE 6

3-{2-[7-(2-(7-Chloro)quinolinyl)heptyl]phenyl} propenoic acid

3-{2-[7-(2-(7-Chloro)quinolinyl)heptyl]phenyl} propenoic acid. A solution of methyl 3-{2-[7-(2-(7-chloro)quinolinyl)-heptyl]phenyl}propenoate (1.0 g, 2.5 mmol) and sodium hydroxide (0.3 g, 7.5 mmol) in 1:1 water/ethanol (20 mL) was stirred at room temperature overnight. The reaction mixture was concentrated under reduced pressure and diluted with water (20 mL). The pH was adjusted to 3–4 using 3N HCl, and the solution was extracted with ethyl acetate. The organic extract was washed with saturated aqueous sodium chloride and dried (MgSO$_4$). The solvent was removed in vacuo to provide a pale yellow oil.

250 MHz $^1$H NMR (CDCl$_3$): δ 8.35–7.00 (m, 10H); 6.40 (d, J=16 Hz, 1H); 2.90 (t, J=9 Hz, 2H); 2.60 (t, J=8 Hz, 2H); 1.90–1.20 (m, 10H).

EXAMPLE 7

5-{2-[7-(2-(7-Chloro)quinolinyl)heptyl]phenyl]-4,6-dithianonanedioic acid

5-{2-[7-(2-(7-Chloro)quinolinyl)heptyl]phenyl]-4,6-dithianonanedioic acid. To a solution of 2-[7-(2-chloroquinolinyl)]heptylbenzaldehyde (0.20 g, 0.5 mmol) and 3-mercaptopropanoic acid (0.12 g, 1.2 mmol) in CH$_2$Cl$_2$ (5 mL) at 0° C. under an argon atmosphere was added dropwise boron trifluoride etherate (0.23 g, 2.0 mmol). The resulting mixture was stirred at 0° C. for 3 h and then extracted with water. The organic extract was dried (MgSO$_4$). The solvent was removed in vacuo to give a yellow oil which was treated with 1M piperazine in isopropanol (0.6 mL), providing a white solid: m.p. 121°–123° C.

EXAMPLE 8

Formulations for pharmaceutical use incorporating compounds of the present invention can be prepared in various forms and with numerous excipients. Examples of such formulations are given below.

Inhalant Formulation

A compound of formula I, 1 to 10 mg/ml, is dissolved in isotonic saline and aerosolized from nebulizer operating at an air flow adjusted to deliver the desired amount of drug per use.

| | Tablets | | |
|---|---|---|---|
| | Ingredients | Per Tablet | Per 10,000 Tablets |
| 1. | Active ingredient (Cpd of Form. I) | 40 mg | 400 g |
| 2. | Corn Starch | 20 mg | 200 g |
| 3. | Alginic acid | 20 mg | 200 g |
| 4. | Sodium alginate | 20 mg | 200 g |
| 5. | Mg stearate | 1.3 mg | 13 g |
| | | 101.3 mg | 1013 g |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 410° F. (60° C.) until dry.

Step 5 Step dry granules are lubricated with ingredient No. 5.

Step 6 The lubricated granules are compressed on a suitable table press.

| | Suppositories: | | |
|---|---|---|---|
| | Ingredients | Per Supp. | Per 1000 Supp. |
| 1. | Formula I compound Active ingredient | 40.0 mg | 40 g |
| 2. | Polyethylene Glycol 1000 | 1350.0 mg | 1,350 g |
| 3. | polyethylene glycol 4000 | 450.0 mg | 450 g |
| | | 1840.0 mg | 1,840 g |

Procedure:

Step 1. Melt ingredient No. 2 and No. 3 together and stir until uniform.

Step 2. Dissolve ingredient No. 1 in the molten mass from Step 1 and stir until uniform.

Step 3. Pour the molten mass from Step 2 into suppository moulds and chill.

Step 4. Remove the suppositories from moulds and wrap.

What is claimed is:

1. A compound of formula I

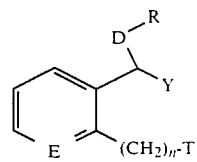

or a pharmaceutically acceptable salt thereof wherein
E is CH or N;

D is O or $S(O)_q$ is 0, 1 or 2;

R is $-(CH_2)_nA$, $-(CH_2)_nArA$ or ArA where n is 1-4, Ar is phenyl or substituted phenyl, thienyl, pyridyl, imidazolyl, tetrazol-5-yl or thiazolyl and A is $-(CH_2)_nR_2$, $-R_2$, $-CN$, $-SO_3H$, $-SO_2NH_2$, $NHSO_2R_6$, $-CH(NH_2)COR_4$, or $-CONHCH_2COR_4$;

Y is $R_2$, $CH(R_3)(CH_2)_mR_2$, $CH(R_3)$-tetrazol-5-yl, or tetrazol-5-yl;

m is 0, 1, and 2;

$R_3$ is hydrogen, $C_1$ to $C_4$ alkoxy, fluoro or hydroxy;

$R_2$ is $-COR_4$ where $R_4$ is $-OH$, $-OE$ where E is a pharmaceutically acceptable cation or a pharmaceutically acceptable ester-forming group, $R_2$ is $-CON(R_5)_2$ where $R_5$ is H, $C_1$ to $C_6$ alkyl, phenyl$C_1$-$C_6$-alkyl, or the two $R_5$ groups are combined to form a cyclic group having 3 to 5 carbons, $-SO_3H$, $-SO_2NH_2$, $NHSO_2R_6$, $-CH(NH_2)COR_4$, or $-CONHCH_2COR_4$;

$R_6$ is $C_1$ to $C_{10}$-alkyl, phenyl, or phenyl$C_1$ to $C_3$-alkyl.

n is 4-11; and

T is halosubstituted quinolyl.

2. A compound of claim 1 where E is CH, D is $-S-$, R is $-CH_2CH_2R_2$, Y is $CH_2R_2$, and n is 4-11.

3. A compound of claim 2 where $R_2$ is $CO_2R_4$, n is 7 and T is 7-chloroquinol-2-yl.

4. A compound of claim 3 which is 3-{2-[7-(7-chloro)quinolin-2-yl)heptyl]phenyl}-3,3'-thiodipropionic acid or a pharmaceutically acceptable salt thereof.

5. A compound of claim 1 where D is $-S-$, R is $-CH_2CH_2R_2$, Y is $CH(OH)R_2$, and n is 4-11.

6. A compound of claim 5 where $R_2$ is $CO_2R_4$, n is 7 and T is 7-chloroquinol-2-yl.

7. A compound of claim 6 which is 2-hydroxy-3-{2-[7-(7-chloro)quinolin-2-yl)heptyl]phenyl}-3,3'-thiodipropionic acid or a pharmaceutically acceptable salt thereof.

8. A compound of claim 1 where D is $-S-$; R is $-(CH_2)_nArA$, where A is $-(CH_2)_nR_2$ or $-R_2$; Y is $CH(R_3)(CH_2e_mR_2$ where $R_3$ is H or $-OH$ and m is 0.

9. A compound of claim 1 where D is $-S-$; R is ArA where A is $-(CH_2)_nR_2$ or $-R_2$; Y is $CH(R_3)(CH_2)_mR_2$ where $R_3$ is H or $-OH$ and m is 0.

10. A compound of claim 1 where E is N, D is $-S-$, R is $-CH_2CH_2R_2$, Y is $CH_2R_2$, and n is 4-11.

11. A compound of claim 10 which is 3-{2-[7-(7-chloro)quinolin-2-yl)heptyl]pyridyl}-3,3'-thiodipropionic acid, or a pharmaceutically acceptable salt thereof.

12. A compound of claim 10 which is 2-hydroxy-3-{2-[7-(2-(7-chloro)quinolinyl)heptyl]pyridyl}-3,3'-thiodipropionic acid or a pharmaceutically acceptable salt thereof.

13. A compound of claim 1 where D is $-O-$.

14. A pharmaceutical composition comprising a compound of claim 1 and a pharmaceutically acceptable excipient.

15. A pharmaceutical composition according to claim 14 in a form suitable for administration by inhalation, parenteral administration, oral administration or topical administration.

16. A pharmaceutical composition according to claim 15 in which the active ingredient is 2-hydroxy-3-{2-[7-(7-chloro)quinolin-2-yl)heptyl]phenyl}-3,3'-thiodipropionic acid or 3-{2-[7-(7-chloro)quinolin-2-yl)heptyl]phenyl}-3,3'-thiodipropionic acid or a pharmaceutically acceptable salt thereof.

17. A pharmaceutical composition for inhibiting antigen-induced respiratory anaphylaxis comprising a pharmaceutical carrier or diluent and an amount of a compound of claim 1 and an $H_1$ blocker sufficient to inhibit said anaphylaxis.

18. A method of treating a pulmonary disease in which leukotrienes are a factor in a subject in need thereof comprising administering to such subject an effective amount of a compound of claim 1 either alone or in combination with a pharmaceutically acceptable excipient.

19. The method of claim 18 in which the pulmonary disease is asthma.

20. A method of treating a non-pulmonary disease in which leukotrienes are a factor in a subject in need thereof comprising administrating to such subject an effective amount of a compound of claim 1 either alone or in combination with a pharmaceutically acceptable excipient.

* * * * *